United States Patent [19]

Barberet et al.

[11] Patent Number: Plant 6,275

[45] Date of Patent: Sep. 6, 1988

[54] CARNATION VARIETY 'LONDIKAY'

[75] Inventors: Nicole Barberet; Yves Ducloux, both of Antibes, France

[73] Assignee: Laboratoire de Physiologie Vegetale de la Londe, La Londe, France

[21] Appl. No.: 889,903

[22] Filed: Jul. 28, 1986

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new carnation variety having medium sized, very light pink blooms borne singly on flower stems of medium length, the plant having a recurrent blooming habit and producing flowers profusely in the midseason of spring and fall with a vigorous, upright and rather rigid growth habit with moderately abundant foliage and being rather tolerant to *Fusarium oxysporum.*

1 Drawing Sheet

BACKGROUND OF THE NEW PLANT

This new carnation cultivar is the result of breeding efforts carried on by us at La Londe, Les Maures, France, this new plant originating as a seedling produced by our crossing of selected individually identified plants growing among our stock of plants maintained at La Londe for breeding purposes. This particular seedling was selected by us for propagation and test because of its unusual, very light pink overall coloration which is not seen in other carnation varieties, this seedling having the additional advantages of a vigorous, upright growth habit and a profuse production of blooms. Asexual propagation of this selected seedling was done by means of cuttings at La Londe and the new plant appearing to be so satisfactory to us that we directed continued propagation of the plant through several successive generations, by means of cuttings. This work was done at La Londe, Les Maures, France, and demonstrated to our satisfaction that the distinctive and novel characteristics of the originally selected seedling are now firmly fixed and hold true from generation to generation. This new plant is now being propagated at La Londe by in vitro propagation as well as by cuttings and is also being grown at Antibes, France.

DESCRIPTION OF THE DRAWING

This new carnation variety is illustrated by the accompanying photographic drawing which shows, in full color, a bud and several flowers in various stages of maturity, the colors shown being as nearly true to those specified herein as is reasonably possible to obtain by conventional photographic procedures.

DESCRIPTION OF THE NEW PLANT

The following is a detailed description of our new carnation variety based upon observation of greenhouse grown plants at La Londe early in 1986, as well as at Antibes, the color designations being specified according to The R.H.S. Colour Chart published by The Royal Horticultural Society of London, England.

THE PLANT

Origin: Seedling.

Parentage:

*Seed parent.*—Stock Plant No. 84 07 P.

*Pollen parent.*—Stock Plant No. 70 V 43. These stock plants were selected from our collection of carnation varieties maintained at La Londe for breeding purposes and each is identified in our breeding records maintained at La Londe, France.

Classification:

*Botanic.—Dianthus caryophyllus.*

*Commercial.*—Standard Carnation.

Form: A tall, erect bush having at least four stems emitted near the ground from a main stem having a length of about 15 cm. due to pinching.

Branching character: Few branches.

Growth habit: Vigorous, upright and rather rigid.

Foliage:

*Quantity.*—Moderately abundant.

*Number of leaves.*—More than 120.

*Leaf size.*—About 16.5 cm. long and about 1 cm. wide, in average, at the seventh node.

*Leaf shape.*—Linear with acuminate apex and curved margins.

*Texture.*—Leathery.

*Color.*—Upper side — 189A. Under side — 189A.

*Ribs and veins.*—Hardly noticeable.

*Rachis.*—Hardly noticeable.

THE BUD

Size: Average.

*Diameter.*—About 2.2 cm.

*Length.*—About 2.6 cm.

Form: Ovoid.

Rate of opening: Normal for carnations.

Color of petals:

*When sepals first divide.*—50D (Empire Rose).

*When petals begin to unfurl.*—54D (Spinel Red) and 50D.

Sepals:

*Number.*—Five.

*Shape.*—The sepals are joined at the lower part and the generally ovate upper part terminates in a sharp pointed apex. The sepals are hooded over the bud before dividing and stand up when the flower opens.

*Color.*—Inside — 145D. Outside — 143C and 144D.

*Striae.*—Longitudinal.

Calyx:

*Size.*—Large.
*Shape.*—Bell shaped.
*Splitting.*—The calyx rarely splits.
*Aspect.*—Smooth.

Flower stem:
*Length.*—In average, about 65 cm.
*Character.*—Rigid and erect.
*Color.*—189A.

THE FLOWER

Blooming habit: Recurrent, blooming profusely in the spring, midseason and fall, with a tendency to give fewer blooms in fall.

Size of Bloom: Medium.
*Diameter.*—Averages about 8 cm.
*Depth.*—Averages about 4.5 cm.

Borne: Singly on strong, straight stems.

Shape: Flat when bloom first opens and when the bloom matures.

Petalage:
*Number of petals.*—About 55, in average.
*Arrangement.*—Imbricated.
*Form.*—Fan shaped with rounded edges and finely serrated at apex edges.
*Texture.*—Leathery.
*Appearance.*—Satiny.
*Color.*—All petals are the same color with the main body being 54D shading to 50D at the margins and becoming very light pink or French Rose, 49D, at the edges. The reverse side of the petal is mainly 50D excepting only that the inside petals have a reverse side of a Chinese Rose color, 58D, with 49D at the edges.

Flower stem:
*Length.*—About 65 cm. (in average, when cut at the tenth node).
*Color.*—189A.
*Character.*—Upright and of good strength.

Fragrance: Perceptible.

Persistence: The petals hang on and dry.

Disease resistance: Rather tolerant to *Fusarium oxysporum* as observed I.N.R.A. Antibes, France.

Lasting quality:
*As a cut flower.*—At least ten days in vase keeping.

REPRODUCTIVE ORGANS

Stamsen:
*Number.*—7 to 10.
*Arrangement.*—Around the ovary.
*Anthers.*—Size: Less than 4 mm. Color: Whitish.
*Filaments.*—Length: Averages about 1.1 cm. Color: Whitish.

Pistils:
*Number.*—2 or 3.
*Styles.*—Length: About 2.8 cm. (in average). Color: Whitish.

Stigmas:
*Color.*—Whitish.

Character of ovaries: The ovary is ribbed.

The overall very light pink Empire Rose coloration of the flowers of this new plant with a darker cast of Spinal Red on the interior of the flower and the generally flat form of the bloom present a very attractive appearance either singly or when grouped with other flowers in a vase or basket display.

We claim:

1. A new and distinctive carnation cultivar, substantially as herein shown and described, characterized by the generally very light pink overall flower coloring somewhat modified by a light red shading coming from the interior of the bloom; and by the intermittent but profuse production of flowers on long, strong stems, and its tall, vigorous, upright growth habit with moderately abundant foliage.

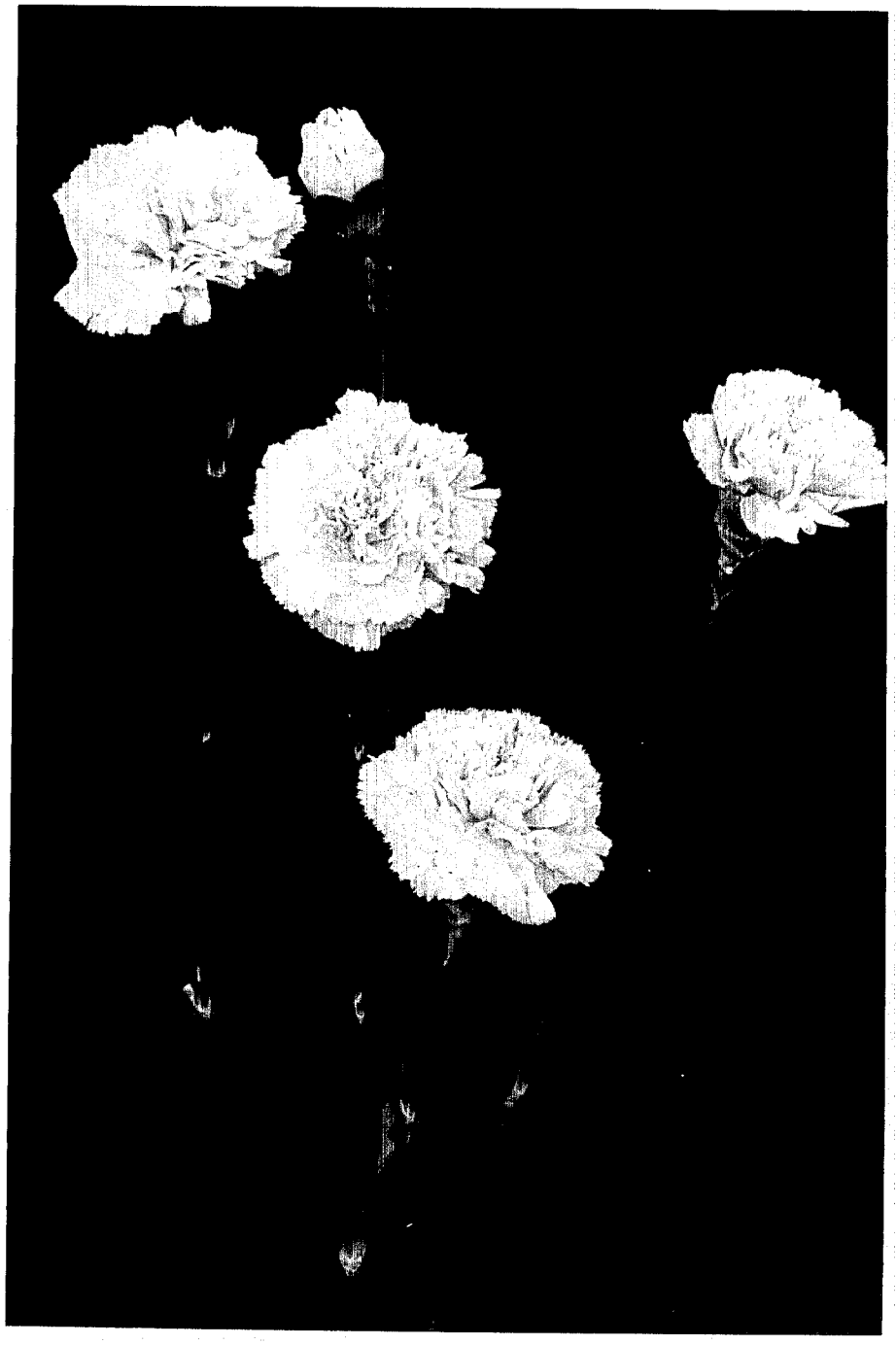

* * * * *